United States Patent [19]

Sheng et al.

[11] 4,144,399

[45] Mar. 13, 1979

[54] CATALYZED DECOMPOSITION OF PEROXIDE INTERMEDIATES RESULTING FROM THE AUTOXIDATION OF ACROLEIN OR METHACROLEIN

[75] Inventors: Ming N. Sheng; Jar-lin Kao, both of Cherry Hill, N.J.

[73] Assignee: Atlantic Richfield Company, Los Angeles, Calif.

[21] Appl. No.: 780,564

[22] Filed: Mar. 23, 1977

[51] Int. Cl.$^2$ .................... C07C 51/00; C07C 57/04
[52] U.S. Cl. .................................................. 562/598
[58] Field of Search .................. 260/526 N, 530 N; 562/598

[56] References Cited

U.S. PATENT DOCUMENTS 2,212,900  8/1940  Groll et al. .................. 260/530 N

*Primary Examiner*—Vivian Garner
*Attorney, Agent, or Firm*—Delbert E. McCaslin

[57] ABSTRACT

A process for the preparation of acrylic acid or methacrylic acid by the ruthenium and/or osmium catalyzed conversion of peroxide (peroxy) intermediate compounds, derived from the autoxidation of acrolein or methacrolein, to the corresponding $\alpha,\beta$-unsaturated carboxylic acid, particularly the conversion of permethacrylic acid and methacrolein monopermethacrylate to methacrylic acid.

13 Claims, No Drawings

CATALYZED DECOMPOSITION OF PEROXIDE INTERMEDIATES RESULTING FROM THE AUTOXIDATION OF ACROLEIN OR METHACROLEIN

BACKGROUND OF THE INVENTION

When $\alpha,\beta$-unsaturated aliphatic aldehydes such as acrolein or methacrolein are oxidized in the liquid phase with oxygen or an oxygen-containing gas such as air, a mixture of products is obtained in the resulting oxidate solution. Based on the total weight, the oxidate solution will generally contain unreacted aldehyde of from 20 to 70 weight per cent, and from 40 to 10 weight percent of the corresponding acid product and peroxide (peroxy) compounds of the unsaturated aldehyde feed materials and peroxide (peroxy) compounds of the unsaturated acid product. The unsaturated peroxide (peroxy) compounds co-produced during the autoxidation of acrolein and methacrolein to acrylic acid and methacrylic acid would be peracrylic acid and acrolein monoperacrylate and permethacrylic acid and methacrolein monopermethacrylate respectively.

The present invention relates to a process for the ruthenium and/or osmium catalyzed conversion or decomposition of the above described unsaturated peroxide compounds formed from the autoxidation of the unsaturated aldehydes (acrolein or methacrolein). The decomposition is carried out after the autoxidation stage is completed. Employment of the ruthenium or osmium catalysts during the oxidation step of the aldehyde does not successfully provide an in situ conversion of the intermediate peroxide compounds to the desired acid product and will cause undesirable and excessive polymerization of the acid product. Thus, while the oxidate product solution of the autoxidation of an aldehyde containing the carboxylic acid product, i.e., acrylic or methacrylic acid, may be treated directly according to the process of this invention, the process to decompose the peroxides is carried out after the aldehyde has been oxidized and the intermediate peroxide compounds formed. Conversion of the peroxide compounds according to this invention provides for a high selectivity to the acid and for the recovery of large percentages of the desired unsaturated carboxylic acid (acrylic or methacrylic) as well as a minimum amount of polymer formation, resulting in high overall yield of the acid from the particular original unsaturated aldehyde as compared to prior art processes, including straight thermal decomposition of peroxide compounds.

U.S. Pat. No. 3,253,025 discloses a process for the preparation of unsaturated aliphatic acids such as methacrylic, by subjecting an oxidate containing peroxides to treatment with a hot liquid solvent of p-toluene sulfonic acid and an alcohol to decompose the peroxides to the acid. However, in this process relatively large percentages of polymer are produced.

An article by Benjamin Phillips et al, Journal of the American Chemical Society, Vol. 76, pp. 5982–5986, 1957 shows the preparation of peracetic acid by the autoxidation of acetaldehyde and with peracetic acid and acetaldehyde monoperacetate as intermediates. At temperatures above 20° C. the acetaldehyde monoperacetate decomposes readily yielding acetic acid. Straight thermal decomposition of the $\alpha,\beta$-unsaturated aliphatic aldehyde peroxy intermediates, such as methacrolein monopermethacrylate and acrolein monoperacrylate does not selectively give high yield of the respective acrylic and methacrylic acids and in addition the rate of reaction is low.

To date no commercially successful process has been developed for the preparation of acrylic acid or methacrylic acid involving the autoxidation of the corresponding $\alpha,\beta$-unsaturated aldehyde and the conversion of the co-produced peroxide intermediate.

The acrylic and methacrylic acid products obtained by the process of this invention have many known commercial uses, particularly for the preparation of esters such as methyl methacrylate and as monomers for polymer formation.

A particular advantage of the process of the present invention is the discovery that catalytic amounts of ruthenium or osmium metal, organic and inorganic ruthenium or osmium compounds or mixtures thereof permit the respective peroxide (peroxy) compounds to be selectively decomposed or converted to the acid, e.g., methacrolein monopermethacrylate to methacrylic acid providing an overall process advantage in the liquid phase autoxidation of the aldehyde.

SUMMARY OF THE INVENTION

According to the present invention there is provided a much improved process for the decomposition of unsaturated peroxide (peroxy) intermediate compounds resulting from the autoxidation of the unsaturated aldehydes acrolein and methacrolein, by converting the respective co-produced peroxides in the oxidate after the autoxidation step to its corresponding unsaturated carboxylic acid, acrylic or methacrylic, at a suitable temperature in the presence of a catalytic amount of a ruthenium and/or osmium catalyst or mixtures thereof.

It is a primary object of this invention to provide a process for the liquid phase preparation of acrylic acid from acrolein or methacrylic acid from methacrolein in high yield by separately converting or decomposing resulting by-product peroxide compounds to the acid and to avoid operational problems associated with prior processes.

It is another object of this invention to provide a novel reaction system useful in the conversion or decomposition of co-produced peroxide intermediate compounds to the desired acid produced by the autoxidation.

It is a further object of this invention to provide a specific mechanism for the employment of ruthenium and/or osmium catalysts for the conversion of peroxide compounds to acids.

These and other objects and advantages of this invention will become apparent from the description of the invention which follows and from the claims.

DESCRIPTION OF THE INVENTION

According to the invention a process has been discovered in which high yield of $\alpha,\beta$-unsaturated aliphatic carboxylic acids may be obtained from the autoxidation of the corresponding $\alpha,\beta$-unsaturated aliphatic aldehyde wherein intermediate unsaturated peroxides are co-produced. Principally, the invention comprises a process of separately and catalytically decomposing the unsaturated peroxide compounds at a suitable temperature in the presence of ruthenium and/or osmium or compounds thereof to obtain increased yield of the acid and avoid the formation of undesired amounts of polymer. After the autoxidation of the unsaturated aldehyde the co-produced peroxide compounds are catalytically decomposed in the oxidate and the oxidate further processed to recover total product acid.

The oxidate including the intermediate peroxide compounds which may be treated according to this invention may be prepared by the oxidation, in the liquid phase, of acrolein or methacrolein to produce acrylic or methacrylic acid. Any method for the preparation of the oxidate which includes the peroxide intermediates may be employed which results in a liquid phase containing any unreacted aldehyde (acrolein or methacrolein), acid product (acrylic or methacrylic acid), peroxides of the aldehyde and the acid (acrolein monoperacrylate and peracrylic acid, and methacrolein monopermethacrylate and permethacrylic acid) together with other by-products such as acetic acid. The unreacted aldehyde (acrolein or methacrolein) may if desired, be distilled from the oxidate prior to or during the catalytic decomposition of the peroxides.

The oxidation process, to produce the acid and peroxide compounds, may be carried out in the liquid phase on the feed acrolein or methacrolein with or without an inert solvent or catalyst in a suitable reactor at temperatures of from about 0° C. to 100° C. and pressures from about atmospheric to 1500 psig by contacting the aldehyde with oxygen or an oxygen-containing gas, such as described, for example, in U.S. Pat. Nos. 3,114,769, 3,155,719 and 3,253,025. The oxidate produced by such processes may be treated by the process of the present invention to convert the intermediate peroxides to the desired acid.

In any liquid phase oxidation process generally about 30 percent of the feed acrolein or methacrolein will be converted to the desired unsaturated product acid and the various peroxides produced will generally be present in the resulting oxidate to from about 5 to 30 weight percent of the total weight of the oxidate.

While lower amounts of polymer formation result from the process of this invention, it is generally desirable, but not essential, to add a polymerization inhibitor to the oxidate. Suitable inhibitors include compounds containing an aromatic nucleus such as hydroquinone, pyrogallol, p-methoxyphenol, cresol, resorcinol and phenol, e.g., 2,6-di-tert-butyl-4-methylphenol. The amount of inhibitor added may be between about 0.01 and 1.0 weight percent of the oxidate.

The catalysts which may be utilized in the process of this invention are ruthenium and osmium metal or an organic or inorganic ruthenium or osmium compound or mixtures thereof. Any organic or inorganic ruthenium or osmium salt having an anion which does not unduly retard the formation of the desired products by an extraneous side reaction can be utilized as a catalyst.

Representative ruthenium catalysts, in addition to ruthenium metal per se include, for example, salts of fatty acids such as ruthenium formate, acetate, propionate and butyrate. Inorganic ruthenium salts such as the halides and oxides are particularly preferred, e.g., ruthenium trichloride and ruthenium dioxide. In addition, organo-metallic compounds such as the ruthenium carbonyls may be employed, e.g. $Ru(CO)_5$, $Ru_2(CO)_9$, $[Ru(CO)_4]_3$, $Ru(CO)X$ wherein X is chlorine, bromine or iodine. Ruthenium chelates having a donor atom selected from the group VA and group VIA elements of the Periodic Table may also be employed in the process. Ruthenium trichloride, ruthenium dioxide and the ruthenium carbonyls are the preferred ruthenium catalysts.

Representative osmium catalysts, in addition to osmium metal per se include, for example, inorganic osmium salts such as osmium dichloride, trichloride, tetrachloride, hexafluoride, tetrafluoride, iodide, disulfide, tetrasulfide, sulfite, dioxide, tetraoxide and sesquioxide. Organo-metallic compounds such as the osmium carbonyls may be used, e.g., osmium dodecacarbonyl and osmium carbonylchloride. In addition osmium chelates having a donor atom from group VA, VIA and VIIA elements of the Periodic Table, such as for example, potassium hexacyanoosmate (IV), hexamine osmium (III) chloride, trispyridine osmium (III) bromide, potassium nitridopentachloroosmate (VI), tris(diethylphenylphosphine) osmium (III) chloride, dipotassium dihydroxosmate and potassium hexa(halo)osmates may be employed in the process of this invention. The preferred osmium catalysts are osmium dioxide, osmium tetrachloride and osmium dodecacarbonyl.

The ruthenium and osmium catalysts may be present in solution or suspension and may also be on support materials which will not affect the decomposition of the peroxide compounds or react with the other products of the oxidate such as alumina, silica gel, aluminosilicates, activated carbon or zeolites. The catalysts may be partially or completely soluble under process conditions and are preferably in a finely divided state.

The decomposition reaction is carried out in the presence of a catalytic proportion of the ruthenium or osmium catalysts and will proceed with small amounts of the representative compounds or metal per se as hereinabove described. Generally the amount of catalyst employed in accordance with the present invention will be equivalent to between about 0.0001 and 1.0 percent by weight and preferably between about 0.01 and 0.20 percent by weight of the oxidate reaction mixture containing the peroxide compounds to be decomposed.

While not essential inert organic solvents may be employed in the process of this invention. The oxidate solution containing the peroxides which may already contain a solvent employed during oxidation may be employed directly in the process of this invention provided the solvent is inert under the reaction conditions used; additional inert solvent may also be added. If the solvent contained in the oxidate is not inert but reactive under the certain decomposition process conditions, e.g., an aromatic hydrocarbon, such as benzene, the solvent may be removed, for example, by distillation, and a non-reactive (inert) solvent added, and the mixture subjected to catalytic decomposition by the process of this invention.

The inert solvents employed are preferably easily separable from the reaction mixture and components thereof including any starting aldehyde, intermediate products and acid product. The solvents which may be employed in concentrations of from about 10 to 95 weight percent, preferably 20 to 80 weight percent of the solvent-oxidate mixture and suitable for use in the process of this invention can be aliphatic, and cycloaliphatic hydrocarbons having from 5 to 16 carbon atoms including halogenated hydrocarbons, ethers and esters. Representative solvents which are especially suitable for use in this invention include, for example, hexane, cyclohexane, n-decane, n-dodecane, ethylcyclohexane, pentane, heptane, carbon tetrachloride, chloroform, methylene chloride, ethyl acetate, butyl acetate, methyl acetate, cyclohexyl acetate, tetrahydrofuran, dioxane, diglyme, etc. Mixtures of solvents may be employed, however, it is preferable to use individual solvents in order to lessen any recovery problems.

The process for the decomposition of the peroxides may be carried out at temperatures of from about ambient about (25° C.) to 100° C. and preferably at temperatures of from about 30° C. to 60° C. The process may be conducted at atmospheric, sub-atmospheric or superatmospheric pressures. However, atmospheric pressure is preferred and provides the best result.

The process of the invention may be carried out batchwise, semi-continuous or continuous in any suitable reactor. A general procedure for carrying out the process of the invention is to add the catalyst to the oxidate reaction product containing the peroxide (peroxy) compounds and heat the mixture to the desired temperature for the appropriate period. The reaction products, after decomposition of peroxides, may be recovered and treated by any conventional method such as, for example, by distillation, by extracting the acid with a base and subsequent acidification, or by solvent extraction.

The reaction time to catalytically decompose the peroxide compounds to the respective unsaturated acid may vary between a few minutes and several hours and is generally dependent on the peroxide being reacted, temperature of reaction and whether the process is continuous or batch.

The following examples are provided to illustrate the invention in accordance with the principles of this invention but are not to be construed as limiting the invention in any way except as indicated by the appended claims. Unless otherwise noted, percentages are in terms of percent by weight.

In the Examples which follow, the feed material for the conversion of the peroxide (peroxy) compounds to acrylic acid or methacrylic acid by the process of this invention were obtained by the autoxidation of acrolein or methacrolein. The unsaturated aldehyde was charged to a suitable reactor (polytetrafluoroethylene-lined stainless steel autoclave or aluminum autoclave) along with a solvent. The mixture was stirred and heated at 45° C. under a pressure of 200 psig air. Oxygen was added whenever there was a 5 psig pressure drop. After 40 psig of oxygen was reacted, the mixture was cooled and the pressure slowly vented. The reaction product (oxidate) and a wash solvent was recovered from the autoclave and a polymerization inhibitor added and subjected to a catalytic decomposition of the peroxides by the process of this invention. Example 4 is a comparative example.

Analysis of the oxidate solution and the decomposition reaction product were conducted as follows: Samples were titrated by differential potassium iodide to determine permethacrylic acid and methacrolein monopermethacrylate or peracrylic acid and acrolein monoperacrylate. Samples were also reduced with triphenylphosphine and analyzed by gas-liquid chromatography to determine any methacrolein or acrolein content, as well as methacrylic or acrylic acid and acetic acid content.

In the Examples the following abbreviations are used:

MA — methacrolein
MAA — methacrylic acid
PMAA — permethacrylic acid
MMPM — methacrolein monopermethacrylate
EMA — ethyl methacrylate
$K_2OsCl_6$ — potassium hexachloroosmate
$Ru_3(CO)_{12}$ — ruthenium carbonyl

EXAMPLE 1

23.0 g. of methacrolein and 52.0 g. of n-hexane was charged to a 550 ml. tetrafluoroethylene (Teflon) lined stainless steel autoclave equipped with a stirrer. The mixture was stirred and heated to 45° C. under 200 psig air. After 5 psig of pressure drop oxygen was added to the autoclave until 40 psig oxygen was reacted. The reactor was cooled and the autoclave vented and the reaction product oxidate washed with 110 ml. of n-hexane. 0.5 g. of 2,6-di-tert-butyl-4-methylphenol was added to inhibit polymerization. The oxidate contained a mixture of methacrolein, permethacrylic acid, methacrolein monopermethacrylate, hexane solvent, acetic acid, methacrylic acid product and minor amounts of other by-products. 3.0 g. portions of the reaction product oxidate containing 0.005 g. of ruthenium carbonyl were heated with stirring on a constant temperature bath to catalytically decompose the peroxide compounds. Similar portions of oxidate to which no catalyst was added were heated for comparison. The results are summarized in Table I which clearly shows the advantages and effects of catalytic decomposition over straight thermal treatment.

TABLE 1

| | Catalytic Decomposition of Peroxide Compounds (MMPM & PMAA) | | | | | |
|---|---|---|---|---|---|---|
| Run No. | Solvent | Catalyst (g.) | Temp. (° C.) | Time (hrs.) | % Peroxide[2] Decompositon | % Selectivity[3] to MAA |
| 1 | n-hexane | $Ru_3(CO)_{12}$ (.005 g.) | 30 | 4 | 29 | 100 |
| 2 | n-hexane | $Ru_3(CO)_{12}$ (.005 g.) | 50 | 2 | 82 | 84 |
| 3[1] | n-hexane | none | 30 | 2 | 1 | —(negligible) |
| 4[1] | n-hexane | none | 50 | 6 | 15 | —(Negligible |

[1] Comparative-no ruthenium or osmium catalyst added.
[2] Original reaction product oxidate contained 1.33 millimoles of PMAA and 44.54 millimoles of MMPM.
[3] Selectivity was calculated on basis of the stoichiometry that MMPM yields two moles of methacrylic acid during decomposition.

EXAMPLE 2

The procedure of Example 1 for the autoxidation of methacrolein to form an oxidate was repeated with the exception that diglyme was used as the wash solvent solution to recover the oxidate reaction product from the autoclave. A 3.0 g. portion of the oxidate containing a mixture of n-hexane and diglyme solvents and 1.43 millimoles of PMMA and 47.20 millimoles of MMPM was heated with stirring to 50° C. for 2 hours in the presence of 0.067 percent by weight of ruthenium carbonyl ($Ru_2(CO)_9$). Analysis of the decomposition product showed a 58 percent peroxide conversion with a 72 percent selectivity to MAA.

EXAMPLE 3 solvents were employed. The results including reaction conditions are summarized in Table 4.

TABLE 4

Catalytic Decomposition of the Peroxy Compounds

| Run No. | Solvent | Catalyst | Conc.[2] Wt. % | Time hr. | Temp. °C. | % MA[3] Conversion | % Peroxy Compound[4] Conversion | MAA | Selectivity[5] to PMAA | MMPM |
|---|---|---|---|---|---|---|---|---|---|---|
| 1 | n-dodecane | $RuO_2$ | 0.10 | 3 | 50 | 25 | 94 | 77 | 1 | 3 |
| 2 | $CCl_4$ | $RuCl_3$ | 0.16 | 2 | 60 | 23 | 93 | 74 | 1 | 4 |
| 3 | $CHCl_3$ | Ru (metal) | 0.08 | 3 | 50 | 23 | 80 | 72 | 2 | 5 |
| 4[1] | n-hexane | $Ru_3(CO)_{12}$ | 0.16 | 3 | 50 | 26 | 97[6] | 80 | 1 | 2 |
| 5 | n-hexane | $OsO_2$ | 0.17 | 3 | 50 | 24 | 95 | 76 | 1 | 4 |
| 6 | n-hexane | $Os_3(CO)_{12}$ | 0.15 | 3 | 50 | 23 | 94 | 76 | 1 | 4 |
| 7 | $CCl_4$ | $K_2OsCl_6$ | 0.35 | 3 | 60 | 24 | 92 | 75 | 1 | 5 |
| 8[1] | n-decane | $OsO_2$ | 0.22 | 2 | 50 | 25 | 95[6] | 78 | 1.5 | 2 |
| 9 | $CHCl_3$ | Os (metal) | 0.11 | 4 | 50 | 24 | 81 | 70 | 2 | 5 |
| 10 | cyclohexane | $OsCl_4$ | 0.16 | 3 | 60 | 26 | 90 | 74 | 1 | 4 |

[1]Acrolein was used to replace methacrolein resulting in co-production of peracrylic acid, 10.6 millimoles and acrolein monoperacrylate, 35.8 mmoles including 8.94 mmoles of acrylic acid.
[2]The concentration was calculated on the basis of the total charge of oxidate.
[3]Total conversion of MA including 1st stage oxidation and subsequent decomposition of peroxides.
[4]The peroxy compounds are permethacrylic acid and methacrolein monopermethacrylate. The original reaction product contained 13.60 mmole of permethacrylic acid, 46.10 mmole of methacrolein monopermethacrylate, and 9.82 mmole of methacrylic acid.
[5]Total selectivity to MAA including oxidation of aldehyde and decomposition of co-produced peroxides.
[6]Peroxy compounds are peracrylic acid and acrolein monoperacrylate.

The procedure of Example 1 for the autoxidation of methacrolein was repeated employing a 700 ml. aluminum reactor. The resulting oxidate contained 1.39 millimoles of PMAA and 45.10 millimoles of MMPM. 3.0 g. portions of the oxidate were heated with stirring to 50° C. in the presence of 0.16 percent by weight concentration of ruthenium carbonyl, $Ru_3(CO)_{12}$, catalyst. Analysis of the decomposition product by iodometry and gas-liquid chromatograph are summarized in Table 2.

TABLE 2

Catalyst Decomposition of MMPM and PMAA Peroxide Compounds

| Run No. | Solvent | Time (Min.) | % MA[2] Conversion | % Peroxide[3] Decomposition | MAA | Selectivity to[4] PMAA | MMPM |
|---|---|---|---|---|---|---|---|
| 1[1] | n-hexane | — | 23 | 0 | 13 | 18 | 61 |
| 2 | n-hexane | 90 | 24 | 84 | 66 | 1 | 13 |
| 3 | n-hexane | 180 | 28 | 94 | 77 | 1 | 4 |

[1]Comparative-no ruthenium or osmium catalyst added.
[2]Total conversion of MA including 1st stage autoxidation and subsequent decomposition of peroxides PMAA and MMPM.
[3]Peroxide compounds are MMPM and PMAA.
[4]Total selectivity to MAA including autoxidation of aldehyde (methacrolein) and decomposition of co-produced peroxides.

EXAMPLE 4 (Comparative)

The experimental procedure described in Example 1 of the U.S. Pat. No. 3,253,025 was carried out. The results are shown in Table 3 wherein a large percentage of polymer rather than methacrylic acid was obtained.

TABLE 3

Decomposition of Peroxy Compounds

| Oxidate Reaction Product | Concentration of Peroxides (mole/l.) | % MA[1] Conversion | Selectivity to[2] MAA | EMA | PMAA | MMPM | Residue (wt. %) in Oxidate |
|---|---|---|---|---|---|---|---|
| Run Product (oxidate) | 0.83 | 31 | 0 | 0 | 1 | 43 | — |
| After Distillation | 0.0 | 30 | 15 | 2 | 0 | 0 | 17[3] |

[1]Total Conversion of Methacrolein
[2]Total Selectivity to Various Products
[3]Polymer formed by Distillation

EXAMPLE 5

A number of decomposition runs were carried out using 3.0 g. samples of an acrolein or methacrolein oxidation product oxidate prepared by the procedure of Example 1. Various ruthenium or osmium catalysts and solvents were employed. The results including reaction conditions are summarized in Table 4.

We claim:
1. A two stage process for the preparation of acrylic acid or methacrylic acid which comprises the steps of:
oxidizing acrolein or methacrolein with oxygen or an oxygen-containing gas in the liquid phase to produce a reaction product oxidate solution containing the corresponding peracrylic acid and acrolein monoperacrylate or permethacrylic acid and methacrolein monopermethacrylate;
subjecting the oxidate solution to a temperature in the range of from about ambient to about 100° C., in the presence of from about 0.0001 to about 1.0 percent by weight of the reaction product oxidate solution of a ruthenium of osmium catalyst selected from the group consisting of ruthenium metal, ruthenium formate, ruthenium acetate, ruthenium propionate, ruthenium butyrate, ruthenium halides, ruthenium oxides, ruthenium carbonyls, osmium metal, osmium dichloride, osmium trichloride, osmium tetrachloride, osmium hexafluoride, osmium tetrafluoride, osmium iodide, osmium disulfide, osmium tetrasulfide, osmium sulfite, osmium diox- ide, osmium tetroxide, osmium sesquioxide, osmium carbonyls, potassium hexacyanoosmate (IV), hexamine osmium (III) chloride, trispyridine osmium (III) bromide, potassium nitridopentachloroosmate (VI), tris(diethylphenylphosphine)osmium (III) chloride, dipotassium dihydroxosmate and potassium hexa(halo)osmates, or mixtures thereof, to catalytically decompose the corresponding peracrylic acid and acrolein monoperacrylate or permethacrylic acid and methacrolein monopermethacrylate to acrylic or methacrylic acid;

and recovering the acrylic or methacrylic acid produced by said oxidation and catalytic decomposition.

2. A process according to claim 1 wherein the ruthenium compounds are selected from ruthenium carbonyl, ruthenium dioxide or ruthenium trichloride.

3. A process according to claim 1 wherein the osmium compounds are selected from osmium dioxide, osmium dodecacarbonyl, osmium tetrachloride, or potassium hexachloroosmate.

4. A process according to claim 1 wherein from about 0.01 to about 0.20 percent by weight of the catalyst is employed in the oxidate.

5. A process according to claim 1 wherein an inert organic solvent is employed in the oxidate at concentrations of from about 10 to about 95 weight percent of the solvent-oxidate mixture and is selected from the group consisting of aliphatic and cycloaliphatic hydrocarbons, halogenated hydrocarbons, ethers and esters or mixtures thereof.

6. A process according to claim 5 wherein the concentration of solvent is from about 20 to 80 weight percent of the solvent-oxidate mixture.

7. A process according to claim 5 wherein the solvent is selected from the group consisting of n-hexane, cyclohexane, n-decane, n-dodecane, carbon tetrachloride, chloroform and diethylene glycol dimethyl ether.

8. A process according to claim 1 wherein the decomposition temperature is in the range of from about 30° C. to 60° C.

9. A process according to claim 1 wherein the ruthenium or osmium catalyst is supported.

10. A two stage process for the preparation of acrylic acid which comprises the steps of:

oxidizing acrolein with oxygen or an oxygen-containing gas in the liquid phase to produce a reaction product oxidate containing unreacted acrolein, peracrylic acid, acrolein monoperacrylate, acrylic acid and other by-products;

adding from about 20 to 80 weight percent of an aliphatic or cycloaliphatic hydrocarbon, halogenated hydrocarbon, ether or ester solvent to said oxidate to form a solvent-oxidate mixture;

subjecting the solvent-oxidate mixture to a temperature in the range of from about 30° C. to 60° C. in the presence of from about 0.01 to 0.20 percent by weight of a ruthenium or osmium catalyst selected from the group consisting of ruthenium metal, ruthenium formate, ruthenium acetate, ruthenium propionate, ruthenium butyrate, ruthenium halides, ruthenium oxides, ruthenium carbonyls, osmium metal, osmium dichloride, osmium trichloride, osmium tetrachloride, osmium hexafluoride, osmium tetrafluoride osmium iodide, osmium disulfide, osmium tetrasulfide, osmium sulfite, osmium dioxide, osmium tetroxide, osmium sesquioxide, osmium carbonyls, potassium hexacyanoosmate (IV), hexamine osmium (III) chloride, trispyridine osmium (III) bromide, potassium nitridopentachloroosmate (VI), tris(diethylphenylphosphine)osmium (III) chloride, dipotassium dihydroxosmate and potassium hexa(halo)osmates, or mixtures thereof, to catalytically decompose peracrylic acid and acrolein monoperacrylate to acrylic acid; and recovering said acrylic acid produced by said oxidation and catalytic decomposition.

11. A process according to claim 10 wherein the unreacted acrolein in the reaction product oxidate is removed by distillation prior to or during the decomposition step.

12. A two stage process for the preparation of methacrylic acid which comprises the steps of:

oxidizing methacrolein with oxygen or an oxygen-containing gas in the liquid phase to produce a reaction product oxidate containing unreacted methacrolein, permethacrylic acid, methacrolein monopermethacrylate, methacrylic acid and other by-products;

adding from about 20 to 80 weight percent of an aliphatic or cycloaliphatic hydrocarbon, halogenated hydrocarbon, ether, or ester solvent to said oxidate to form a solvent-oxidate mixture;

subjecting the solvent-oxidate mixture to a temperature in the range of from about 30° C. to 60° C. in the presence of from about 0.01 to 0.20 percent by weight of a ruthenium or osmium catalyst selected from the group consisting of ruthenium metal, ruthenium formate, ruthenium acetate, ruthenium propionate, ruthenium butyrate, ruthenium halides, ruthenium oxides, ruthenium carbonyls, osmium metal, osmium dichloride, osmium trichloride, osmium tetrachloride, osmium hexafluoride, osmium tetrafluoride, osmium iodide, osmium disulfide, osmium tetrasulfide, osmium sulfite, osmium dioxide, osmium tetroxide, osmium sesquioxide, osmium carbonyls, potassium hexacyanoosmate (IV), hexamine osmium (III) chloride, trispyridine osmium (III) bromide, potassium nitridopentachloroosmate (VI), tris(diethylphenylphosphine) osmium (III) chloride, dipotassium dihydroxosmate and potassium hexa(halo)osmates, or mixtures thereof, to catalytically decompose permethacrylic acid and methacrolein monopermethacrylate to methacrylic acid; and recovering said methacrylic acid produced by said oxidation and catalytic decomposition.

13. A process according to claim 12 wherein the unreacted methacrolein in the reaction product oxidate is removed by distillation prior to or during the decomposition step.

* * * * *